US012797616B2

(12) United States Patent
Lambert

(10) Patent No.: US 12,797,616 B2
(45) Date of Patent: Nov. 17, 2026

(54) SYSTEM WITH CHARGING / PATIENT-APPLIED PART PORT

(71) Applicant: Shiratronics, Inc., Brooklyn Park, MN (US)

(72) Inventor: Scott Anthony Lambert, East Bethel, MN (US)

(73) Assignee: Shiratronics, Inc., Brooklyn Park, MN (US)

( * ) Notice: Subject to any disclaimer, the term of this patent is extended or adjusted under 35 U.S.C. 154(b) by 213 days.

(21) Appl. No.: 18/421,143

(22) Filed: Jan. 24, 2024

(65) Prior Publication Data

US 2024/0252823 A1 Aug. 1, 2024

Related U.S. Application Data

(60) Provisional application No. 63/442,190, filed on Jan. 31, 2023.

(51) Int. Cl.
*A61N 1/36* (2006.01)
*A61N 1/378* (2006.01)
*H01R 13/64* (2006.01)

(52) U.S. Cl.
CPC ..... *A61N 1/36075* (2013.01); *A61N 1/36125* (2013.01); *A61N 1/3787* (2013.01); *H01R 13/64* (2013.01); *H01R 2201/12* (2013.01)

(58) Field of Classification Search
CPC .............. A61N 1/36125; A61N 1/3787; A61N 1/37235; A61N 1/37229
See application file for complete search history.

(56) References Cited

U.S. PATENT DOCUMENTS

2009/0118796 A1 5/2009 Chen et al.
2017/0021184 A1* 1/2017 Pavel .................. A61N 1/3987
2018/0021587 A1 1/2018 Strother et al.
2020/0360707 A1 11/2020 Christiansen et al.

OTHER PUBLICATIONS

"International Application Serial No. PCT US2024 012697, International Search Report mailed May 10, 2024", 5 pgs.
"International Application Serial No. PCT US2024 012697, Written Opinion mailed May 10, 2024", 7 pgs.

* cited by examiner

*Primary Examiner* — Brian T Gedeon
(74) *Attorney, Agent, or Firm* — Schwegman, Lundberg & Woessner, P.A.

(57) ABSTRACT

A medical system includes a patient-applied part, a medical device, a power cable, and a patient-applied part cable. The medical device may include a device housing, a rechargeable battery within the device housing, a control circuit within the device housing, a power circuit within the device housing, and an electrical port on the device housing for use in making electrical connections to the control circuit and the power circuit within the device housing. The power cable may have a first end configured to be electrically connected to an electrical power line and a second end configured to be removably connected to the electrical port. The patient-applied part cable may have a first end configured to be electrically connected to the patient-applied part and a second end configured to be removably connected to the electrical port.

20 Claims, 6 Drawing Sheets

SYSTEM WITH CHARGING / PATIENT-APPLIED PART PORT

PRIORITY

This application claims the benefit of priority to U.S. Provisional Patent Application Ser. No. 63/442,190, filed Jan. 31, 2023, which is incorporated by reference herein in its entirety.

TECHNICAL FIELD

This document relates generally to medical systems or devices, and more particularly, but not by way of limitation, to battery powered medical device with a single external electrical connection for non-concurrently charging the battery and interfacing with a patient-applied part.

BACKGROUND

There are standards for medical systems in different environments. For example, the International Electrotechnical Commission (IEC) publishes technical standards for the safety and performance of medical electrical equipment. Other standards exist. IEC standards consider the normal environment of use for the medical system (e.g., healthcare facilities or home healthcare). The standards IEC 60601-1-11 addresses the basic safety and essential performance of medical systems for normal use in the home healthcare environment, regardless of whether the medical systems are operated by a trained or untrained person.

The IEC considers medical equipment to be equipment intended by its manufacture to be used in the diagnosis, treatment or monitoring of a patient, or to be used for the compensation or alleviation of disease, injury or disability. Medical devices may sense signals and/or deliver a therapy. For example, medical devices may include implantable devices configured to deliver a therapy such as an electrical therapy. The medical equipment has an applied part, or transfers energy to or from the patent detects such energy transfer to or from the patient. Medical equipment has an applied part if part of the equipment naturally comes into physical contact with the patient during normal use in order to perform its function. Implantable electrical therapy devices may include implantable neurostimulators. An example of an implantable neurostimulator includes a fully head-located implantable peripheral neurostimulation system, having one or more implantable devices, designed for the treatment of chronic head pain is a specific example of an implantable neurostimulation system. A corresponding coil assembly for each of the implantable devices may be used to interface with the implantable device. The coil assembly may be termed a patient-applied part as it contacts the patient during normal use.

Some considerations for the home environment include the presence of children, pets, liquid spills and untrained users. Another consideration for the home environment is less reliable electrical power wiring. For example, many homes may not have a reliable Earth ground connection. Therefore, the standards may require products to be designed to protect non-professional users from shock. The standards may require additional insulation and other requirements such as a minimum distance between two conductors along the insulating surface ("creepage distance") to protect the user from electrical hazards when the medical equipment is in contact with the patient during normal use.

Known medical devices have separate external connections for power supply/battery charger and for an applied part. This allows the patient to be connected to a medical device that is also connected to AC line power at the same time, but this type of design requires a higher degree of electrical isolation to ensure the patient's safety, which results in larger and more expensive devices. Improvements are desired for medical devices intended for use in healthcare facilities and in the home healthcare environment.

SUMMARY

An example (e.g., "Example 1") of a medical system includes a patient-applied part, a medical device, a power cable, and a patient-applied part cable. The patient-applied part is configured to physically contact a patient during normal use. The medical device may include a device housing, a rechargeable battery within the device housing, a control circuit within the device housing, a power circuit within the device housing, and an electrical port on the device housing for use in making electrical connections to the control circuit and the power circuit within the device housing. The power cable may have a first end configured to be electrically connected to an electrical power line and a second end configured to be removably connected to the electrical port. The patient-applied part cable may have a first end configured to be electrically connected to the patient-applied part and a second end configured to be removably connected to the electrical port. The electrical port is not able to be concurrently connected to both the power cable and the patient-applied part cable. The power circuit is configured to be electrically connected to the electrical power line via the power cable and to recharge the rechargeable battery using power from the electrical power line. The control circuit is configured to be powered by the rechargeable battery and is electrically connected to the patient-applied part via the patient-applied part cable during normal use when the patient-applied part is in physical contact with the patient, thereby enabling the medical system to diagnose, treat or monitor a patient or to compensate or alleviate a disease, an injury or a disability experienced by the patient. The medical system may be designed for use in a home healthcare environment.

In Example 2, the subject matter of Example 1 may optionally be configured such that the patient-applied part includes a coil assembly configured for use to be placed on the patient and used to charge an implantable device.

In Example 3, the subject matter of any one or more of Examples 1-2 may optionally be configured such that the patient-applied part includes a coil assembly configured for use to be placed on the patient and used to communicate with and/or program an implantable device.

In Example 4, the subject matter of any one or more of Examples 1-3 may optionally be configured such that the patient-applied part includes at least one electrode configured to contact the patient.

In Example 5, the subject matter of Example 4 may optionally be configured such that the at least one electrode is used to deliver an electrical therapy to the patient.

In Example 6, the subject matter of any one or more of Examples 4-5 may optionally be configured such that the at least one electrode is used to sense an electrical signal from the patient.

In Example 7, the subject matter of any one or more of Examples 1-6 may optionally be configured such that the at least one electrode is used to sense an electrical signal from the patient.

In Example 8, the subject matter of any one or more of Examples 1-7 may optionally be configured such that the patient-applied part includes a sensor configured to contact the patient during normal use.

In Example 9, the subject matter of any one or more of Examples 1-8 may optionally be configured such that the first end of the patient-applied part cable is integrally connected to the patient-applied part.

In Example 10, the subject matter of any one or more of Examples 1-8 may optionally be configured such that the first end of the patient-applied part cable is removably connected to the patient-applied part.

In Example 11, the subject matter of any one or more of Examples 1-10 may optionally be configured such that the electrical port includes a plurality of conductor connectors. The plurality of conductor connectors may include exclusive first and second subsets. The first subset may be exclusively used to electrically connect the power circuit to the electrical power line via the power cable. The second subset may be exclusively used to electrically connect the control circuit to the patient-applied part.

An example (e.g., "Example 12") of a medical system may include at least one implantable medical device, at least one coil assembly corresponding to the at least one implanted medical device and configured for use to charge, program, and/or communicate with the at least one implantable medical device, and an external medical device. The external medical device may include a device housing, a rechargeable battery within the device housing, a control circuit within the device housing, a power circuit within the device housing, and an electrical port on the device housing for use in making electrical connections to the control circuit and the power circuit within the device housing. The medical system may include a power cable with a first end configured to be electrically connected to an electrical power line and a second end configured to be removably connected to the electrical port, and a coil assembly cable with a first end configured to be electrically connected to the at least one coil assembly and a second end configured to be removably connected to the electrical port. The electrical port is not able to be concurrently connected to both the power cable and the coil assembly cable. The power circuit is configured to be electrically connected to the electrical power line via the power cable and to recharge the rechargeable battery using power from the electrical power line. The control circuit is configured to be powered by the rechargeable battery and is electrically connected to the at least one coil assembly via the coil assembly cable during normal use when the at least one coil assembly is in physical contact with the patient.

In Example 13, the subject matter of Example 12 may optionally be configured such that the at least one implantable device includes an implantable neurostimulator.

In Example 14, the subject matter of any one or more of Examples 12-13 may optionally be configured to further include a headset, where the headset includes the at least one coil assembly.

In Example 15, the subject matter of Example 14 may optionally be configured such that the headset includes at least one sensor. The coil assembly cable may be configured for use to make an electrical connection between the at least one sensor and the control circuit via the electrical port.

In Example 16, the subject matter of any one or more of Examples 14-15 may optionally be configured such that the electrical port includes a plurality of conductor connectors. The plurality of conductor connectors may include exclusive first and second subsets, where the first subset is exclusively used to electrically connect the power circuit to the electrical power line via the power cable, and the second subset is exclusively used to electrically connect the control circuit to the headset.

In Example 17, the subject matter of any one or more of Examples 14-16 may optionally be configured such that the first end of the patient-applied part cable is integrally connected to the headset.

In Example 18, the subject matter of any one or more of Examples 12-17 may optionally be configured such that the second end of the power cable and the second end of the coil assembly have identical connectors to mate with electrical port.

An example (e.g., "Example 19") of a method may be performed in a healthcare facility or home healthcare environment using a medical system having a patient-applied part configured to physically contact a patient during normal use and a medical device. The medical device may include a device housing, a rechargeable battery within the device housing, a control circuit within the device housing, a power circuit within the device housing, and an electrical port on the device housing for use in making electrical connections to the control circuit and the power circuit within the device housing. The method may include electrically connecting the patient-applied part to the control circuit during normal use when the patient applied-part is in physical contact with the patient, thereby enabling the medical system to diagnose, treat or monitor a patient or to compensate or alleviate a disease, an injury or a disability experienced by the patient. A patient applied-part cable may be used to electrically connect the patient-applied part to the control circuit. The patient applied-part cable has a first end configured to be electrically connected to the patient-applied part and a second end configured to be removably connected to the electrical port. The method may include charging the rechargeable battery using a power cable with a first end configured to be electrically connected to an electrical power line and a second end configured to be removably connected to the electrical port to make an electrical connection with the power circuit. The electrical port is not able to be concurrently connected to both the power cable and the patient applied-part cable.

An example (e.g., "Example 20") of a method may be performed using a medical system having a headset with at least one coil assembly configured for use to charge, program, and/or communicate with at least one implantable medical device, and having an external medical device, including a device housing, a rechargeable battery within the device housing, a control circuit within the device housing, a power circuit within the device housing, and an electrical port on the device housing for use in making electrical connections to the control circuit and the power circuit within the device housing. The method may include electrically connecting the headset to the control circuit during normal use when the headset is in physical contact with the patient and is being used to communicate with, program, and/or charge the at least one implantable device. The method may further include charging the rechargeable battery using a power cable with a first end configured to be electrically connected to an electrical power line and a second end configured to be removably connected to the electrical port to make an electrical connection with the power circuit. The electrical port is not able to be concurrently connected to both the power cable and the patient-applied part cable.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
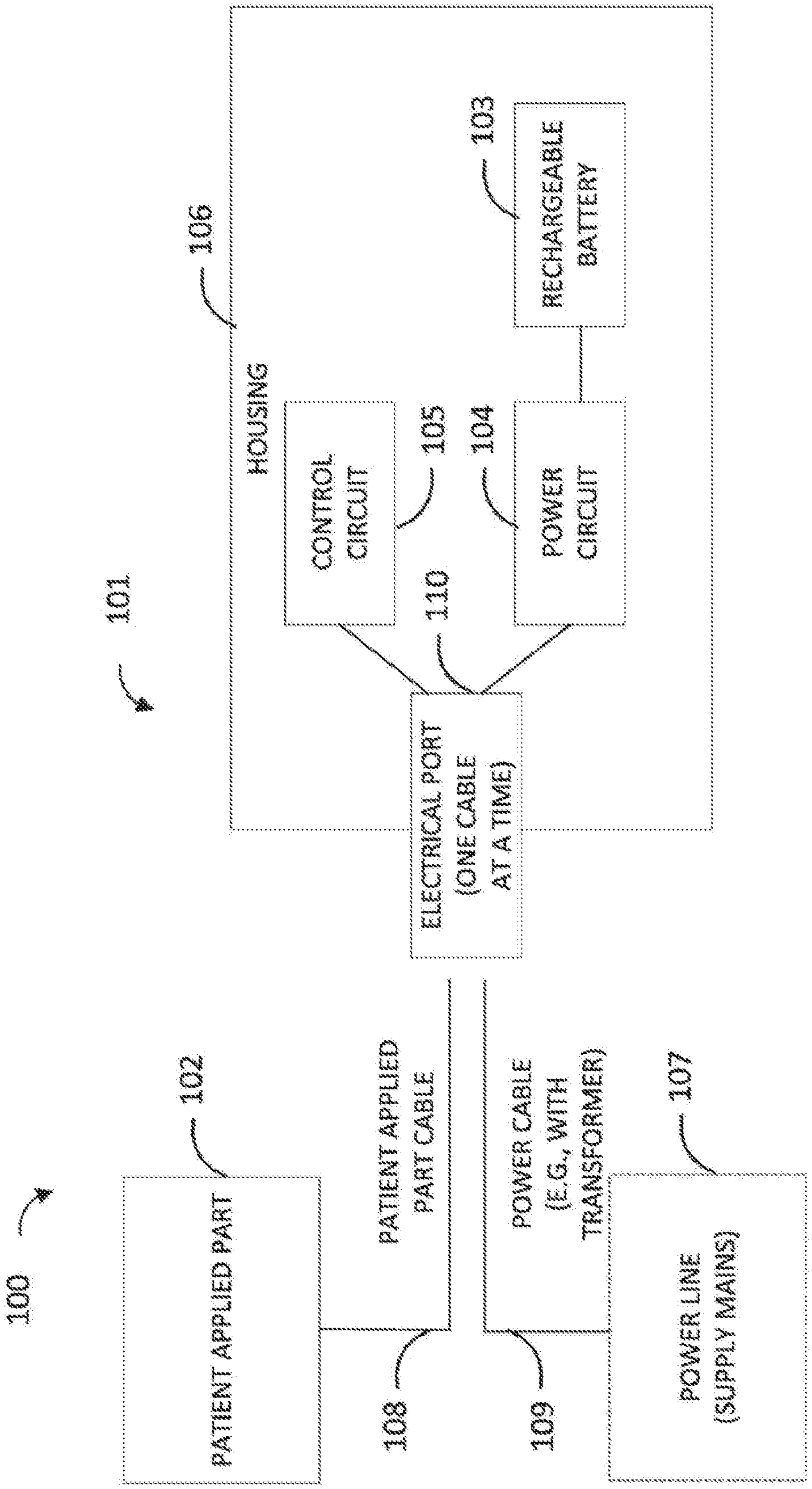
FIG. 1 illustrates, by way of example and not limitation, a medical system that includes a rechargeable battery and one electrical port.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments of the present subject matter provide an improved battery-powered medical device with a single external electrical connection (e.g., port) for use in non-concurrently charging a rechargeable battery in the medical device and interfacing with a patient-applied part. This device design prevents the device from being connected to the patient and to AC line power at the same time. That is, the device cannot be connected to the electrical power wiring in the home to charge the rechargeable battery at the same time that the device is connected to applied parts in physical contact with the patient. Thus, the device may be manufactured smaller and less expensively as there is no need to design the device with the additional insulation and creepage distance to protect the user from electrical hazards.

A medical device, powered by a rechargeable battery, may be connected to a patient-applied part. A battery-powered medical device may need to be periodically recharged. Additionally, the battery-powered medical device may need to facilitate a medical function such as communicating, programming, and/or recharging a medical device implant. Additional protection from electrical shock would be required if the device can be connected to the patient and to AC line power at the same time.

Various embodiments of the present subject matter provide only one external electrical connector for use in charging the rechargeable battery and performing the medical function such as communications, programming, and/or recharging of a medical device implant. Since the external connector is only one connector, the device is only capable of recharging when the device is not connected to the patient-applied part, and is only capable of being connected to the patient-applied part when it is not recharging. Thus, a medical device that is connected the patient-applied part that is in physical contact with the patient cannot also be connected to line power. The single connector reduces the risk of electrical shock to the patient and reduces the electrical isolation required in the battery powered medical device which can result in a smaller and lower cost design.

By way of example and not limitation, a medical device system may include implantable medical device(s) and an external medical device configured for use to communicate with, program, and/or charge the implantable medical device (s). More particularly, the system may include a fully head-located neurostimulator(s) designed for the treatment of chronic head pain. The system may be configured to provide neurostimulation therapy for chronic head pain, including chronic head pain caused by migraine and other headaches, as well as chronic head pain due other etiologies. For example, the system may be used to treat chronic head and/or face pain of multiple etiologies, including migraine headaches; and other primary headaches, including cluster headaches, hemicrania continua headaches, tension type headaches, chronic daily headaches, transformed migraine headaches; further including secondary headaches, such as cervicogenic headaches and other secondary musculoskeletal headaches; including neuropathic head and/or face pain, nociceptive head and/or face pain, and/or sympathetic related head and/or face pain; including greater occipital neuralgia, as well as the other various occipital neuralgias, supraorbital neuralgia, auriculotemporal neuralgia, infraorbital neuralgia, and other trigeminal neuralgias, and other head and face neuralgias. The use of the cable within such a medical system is discussed here. However, the cable may be used with other medical systems.

FIG. 1 illustrates, by way of example and not limitation, a medical system that includes a rechargeable battery and one electrical port. The illustrated medical system 100 includes a medical device 101 and a patient-applied part 102 configured to be in physical contact with the patient during normal use of the medical device 101. The illustrated medical device 101 includes a rechargeable battery 103, a power circuit 104, a control circuit 105, and a housing 106 containing the battery 103, power circuit 104 and control circuit 105. The battery 103 and power circuit 104 are configured to power the medical device 101. The power circuit 104 may be configured to be connected to the power line 107, e.g., via a transformer (not shown) to convert the power line voltage to a lower voltage for the device, to charge the rechargeable battery 103. The control circuit 105 is configured to perform functions for the medical system using the patient-applied part 102 when the patient-applied part is in physical contact with the patient. A patient-applied part physically contacts the patient during normal use of the device. Examples of patient-applied parts include, but are not limited to, electrical contacts (e.g., electrodes) used to deliver an electrical therapy. For example, a transcutaneous electrical nerve stimulation (TENS) system may use electrodes to deliver the TENS therapy. Patient-applied parts may also include electrical contacts to sense electrical signals in the patient, or other sensors. Examples of other sensors include, but are not limited to, temperature sensors, galvanic skin response sensors, pulse oximeters, blood pressure cuffs, and the like. By way of example and not limitation, the patient-applied part 102 may include a coil assembly configured to be positioned in contact with the patient and over a medical device implant, and the control circuit 105 may be configured to communicate, program and/or recharge the medical device implant. A patient-applied part cable 108 may be used to connect the patient-applied part to the medical device and a power cable 109, which may include a transformer, may be used to connect the medical device to the power line 107. The device 101 is designed with one electrical port 110. The proximal ends of both the patient-applied part cable 108 and the power cable 109 may have a same physical connector design for connection to the electrical port 110, but may be configured to contact different conductor connectors in the electrical port.

Figure 2:
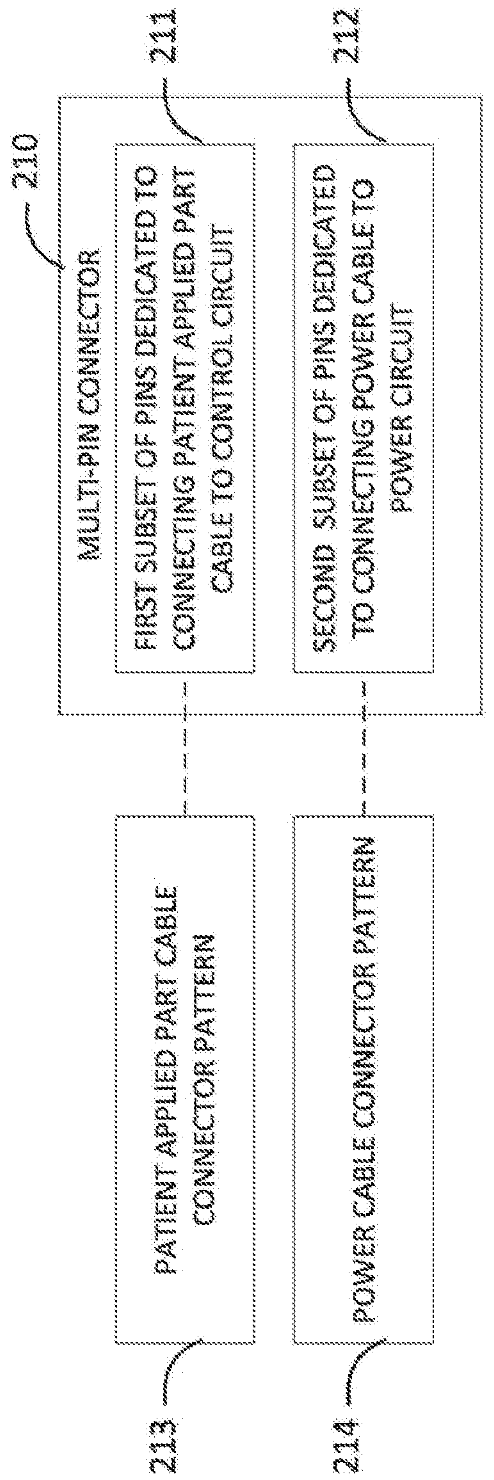
FIG. 2 illustrates, by way of example and not limitation, a multi-pin connector configured for use to provide different connections to a patient-applied part cable and to a power cable.

FIG. 2 illustrates, by way of example and not limitation, a multi-pin connector configured for use to provide different connections to a patient-applied part cable and to a power cable. The illustrated multi-pin connector 210 may be a specific example of an electrical port 110 in FIG. 1, and may include a plurality of pins, including a first subset of pins 211 dedicated to connecting a patient-applied part cable to the control circuit and a second subset of pins 212 dedicated to the power cable to the power circuit. The patient-applied part cable (e.g., patient-applied part cable 108 in FIG. 1) may have a proximal end with a corresponding connector pattern 213 to interface with the first subset of pins 210 so as to allow the controller to interface with the patient-applied part when the patient-applied part cable is in the single electrical port. The power cable (e.g., power cable 109 in FIG. 1) may have a proximal end with a corresponding connector pattern 214 to interface with the second subset of pins 212 so as to allow the power circuitry to be electrically connected to the power in the healthcare facility or home healthcare environment. Therefore, the first subset may be used to exclusively connect the power circuit and the second subset may be used to exclusively connect the control circuit. However, other embodiments may use common connections for the power circuit and control circuit. That is, the first and second subsets of connectors need not be exclusive of each other.

Figure 3:
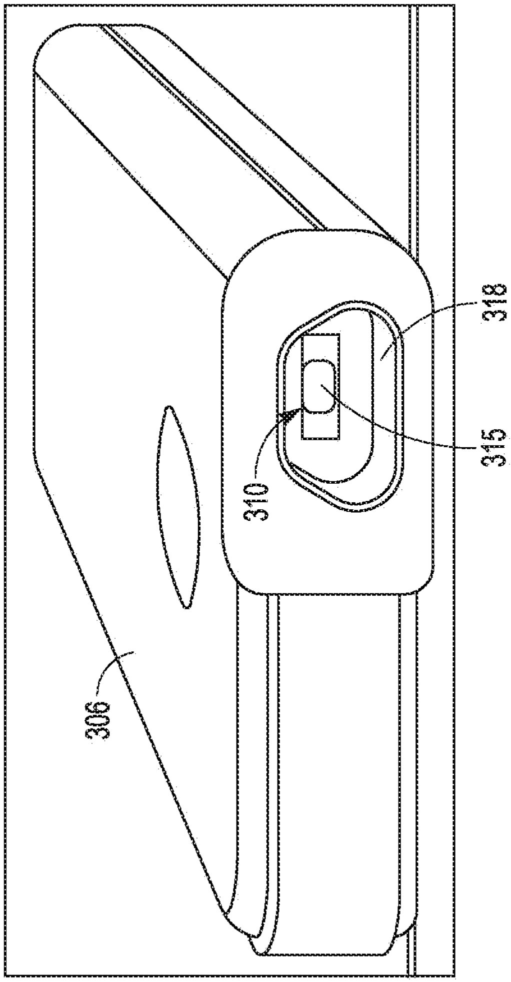
FIG. 3 illustrates, by way of example and not limitation, an example of the housing of the medical device including the single electrical port for use to non-concurrently connect to the power cable and to the patient-applied part cable.
Figure 4:
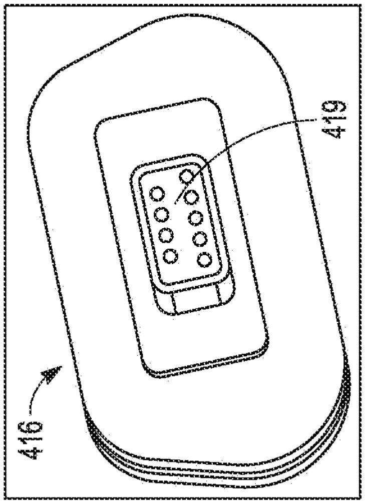
FIG. 4 illustrates, by way of example and not limitation, a connector plug for a power cord.
Figure 5:
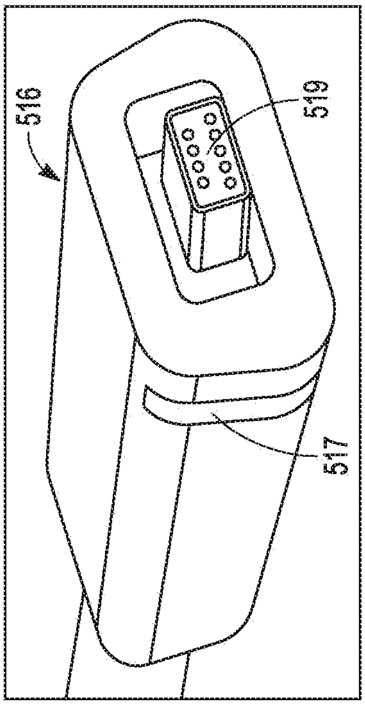
FIG. 5 illustrates, by way of example and not limitation, a connector plug for a patient-applied part.

FIG. 3 illustrates, by way of example and not limitation, an example of the housing of the medical device including the single electrical port for use to non-concurrently connect to the power cable and to the patient-applied part cable. The single electrical port 310 and the device housing 306 may be configured with a shape to only allow certain connector plug shapes to be inserted into the port 310. In the illustrated embodiment, the electrical port includes a 9-pin connector 315. FIG. 4 illustrates, by way of example and not limitation, a connector plug 416 for a power cord, and FIG. 5 illustrates, by way of example and not limitation, a connector plug 516 for a patient-applied part. Each plug 416, 516 has a similar size and shape to be received in the port 310 illustrated in FIG. 3. Further, the connector plugs 416, 516 and port 310 are designed to accept the plugs 416, 516 only in one orientation. The exterior of the plugs may have a groove (e.g., 517) configured to receive a ridge 318 in the housing 306 of electrical device to form a secure connection. In the illustrated embodiment, each of the plugs 416, 516 has nine sockets 419, 519 for receiving the nine pins for the connector 315.

Figure 6:
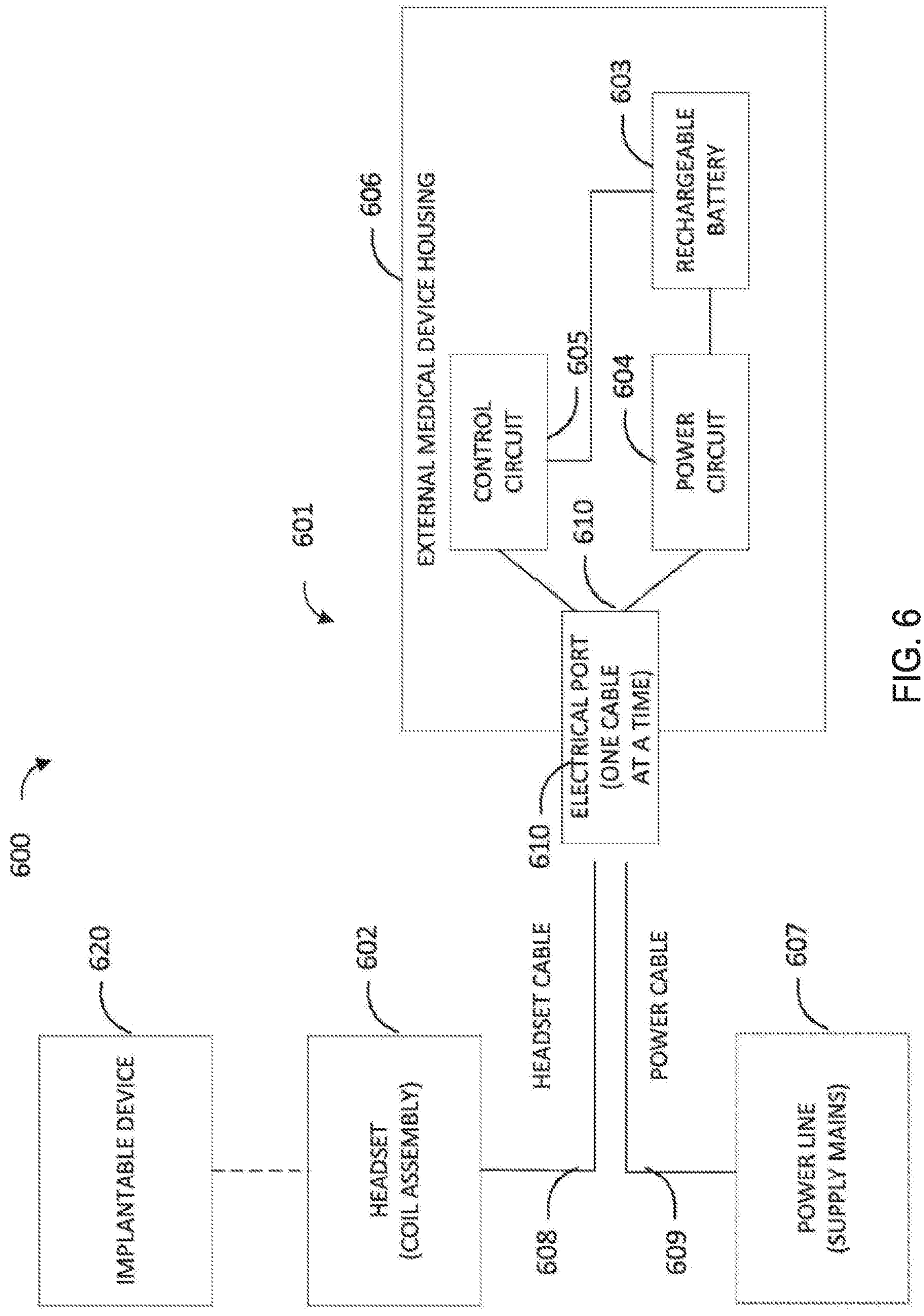
FIG. 6 illustrates, by way of example and not limitation, a specific example in which the medical system illustrated in FIG. 1 includes a headset with at least one coil assembly for interfacing with at least one head-located implantable device.

FIG. 6 illustrates, by way of example and not limitation, a specific example in which the medical system illustrated in FIG. 1 includes a headset with at least one coil assembly for interfacing with at least one head-located implantable device. The illustrated medical system 600 includes an external medical device (e.g., charger) 601 as a specific example of medical device 101 in FIG. 1 and further includes a headset with at least one coil assembly 602 as a specific example of a patient-applied part 102 in FIG. 1. The coil assembly 602 may be used to interface with an implantable device 620. For example, the coil assembly 602 may be used for programming the implantable device, communicating with the implantable device, and charging the rechargeable battery within the implantable device. The headset may include two coil assemblies for interfacing (e.g., programming, communicating and/or charging) with two implantable devices. The illustrated charger 601 includes a rechargeable battery 603, a power circuit 604, a control circuit 605, and a housing 606 containing the battery 603, power circuit 604 and control circuit 605. The battery 603 and power circuit 604 are configured to power the medical device 601. The power circuit 604 may be configured to be connected to the power line 607, e.g., via a transformer (not shown) to convert the power line voltage to a lower voltage for the device, to charge the rechargeable battery 603. The control circuit 605 is configured to perform functions (e.g., programming, communicating and/or charging) for the medical system using the coil assembly when the coil assembly is in physical contact the patient. A headset cable 608 may be used to connect the coil assembly (or coil assemblies) on the headset to the charger and a power cable 609 may be used to connect the charger 601 to the power line 607. The charger 607 is designed with one electrical port 610. The proximal ends of both the headset cable 608 and the power cable 609 may have a same physical connector design for connection to the electrical port 610, but may be configured to contact different conductor connectors in the electrical port (e.g., see FIG. 2).

Figure 7:
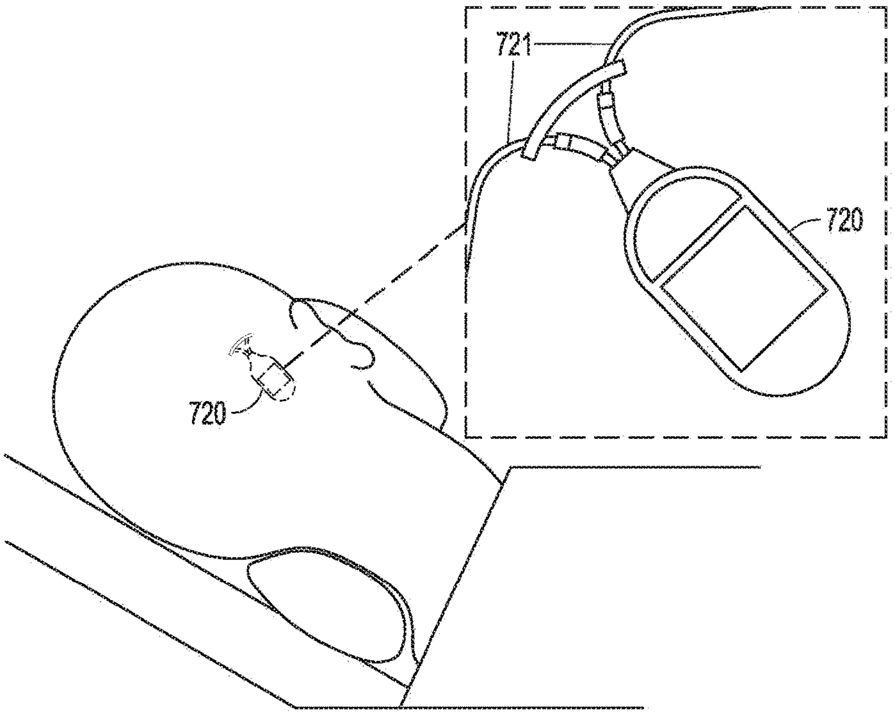
FIG. 7 illustrates, by way of example and not limitation, an implantable medical device implanted beneath the skin and over a patient's cranium.

FIG. 7 illustrates, by way of example and not limitation, an implantable medical device 720 implanted beneath the skin and over a patient's cranium. The device may be referred to as a fully-head-located implantable device. The device 720 is illustrated as being implanted behind and above the car. The implantable medical device 720 may include one or more leads 721 that may be subcutaneously tunneled to a desired neural target. The lead(s) may be integral to the device 720, as they have proximal lead ends that extend into housing of the device where electrical connections are made between stimulator circuitry and electrodes on the lead. When the medical device has integral leads, the leads are not removably connected to the device.

The number of electrodes and spacing may be such as to provide therapeutic stimulation over any one or any combination of the supraorbital, parietal, and occipital region substantially simultaneously. The implantable medical device 720 may be configured to independently control each electrode to determine whether the electrode will be inactive or configured as a cathode or an anode. One or more electrodes on the lead(s) may be configured to function as an anode, and one or more electrodes on the lead may be configured to function as a cathode. For example, bipolar neuromodulation may be delivered using one or more anodes and one or more cathodes on the lead(s). A clinician may program the electrode configurations to provide a neuromodulation field that captures a desired neural target for the therapy.

Figure 8:
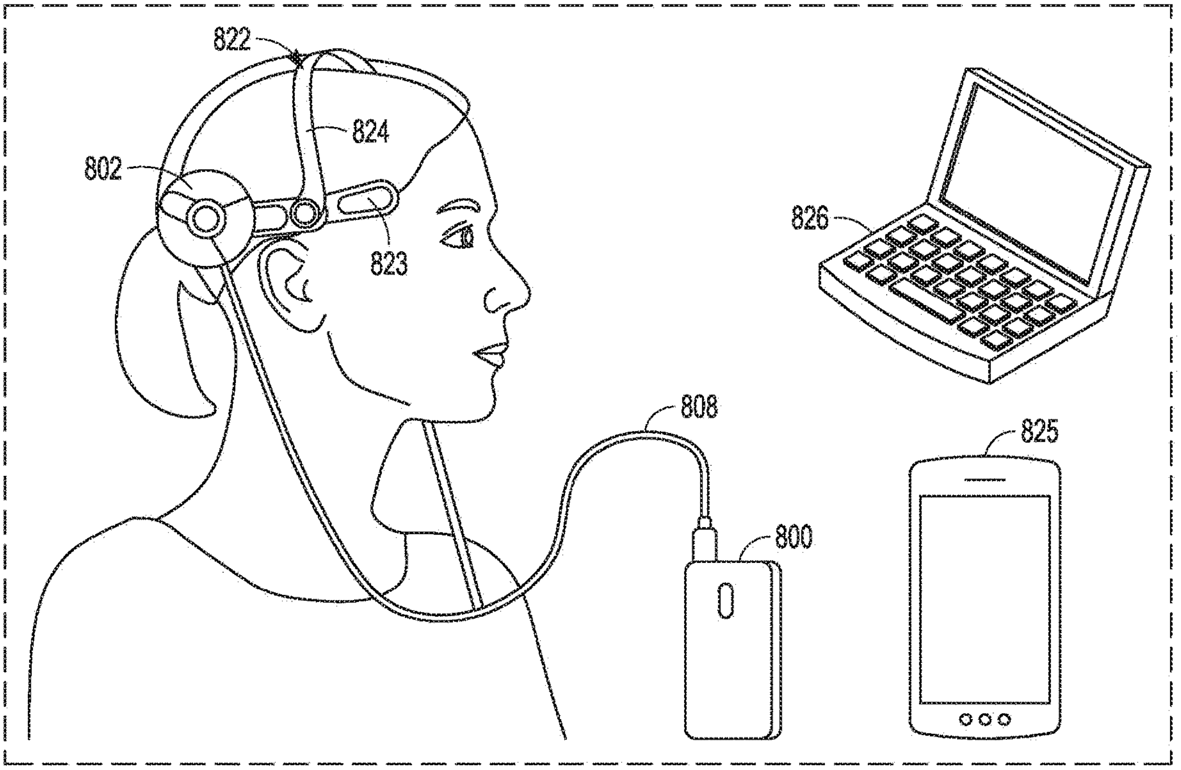
FIG. 8 illustrates, by way of example and not limitation, an external medical device and headset configured for use to communicate with and/or charge the implantable medical device(s).

FIG. 8 illustrates, by way of example and not limitation, an external medical device 800 and headset 822 configured for use to communicate with and/or charge the implantable medical device(s). The headset 822 may include an external coil 802 used to provide the communication/programming/charging functions, and the headset 822 may be configured to position the external coil over an implantable medical device. The headset 822 may include two external coils 802 to be positioned over two implantable medical devices, where one of the implantable medical devices is on each side of the head. The external coils 802 may be considered to be patient-applied parts as these are in contact with the patient during normal use. The headset 822 may include, for example, an adjustable frame 823 on each side of the head that can rotate about a point on a main headset frame 824, and may be configured to provide additional degrees of motion (e.g., sliding or pivoting motion) with respect to the main headset frame 824. These adjustable frames may be used to position the external coils 802 over the implantable medical devices when the main headset frame 824 is worn. The external medical device 800 may be electrically connected to the external coil(s) 802 via a headset cable 808. In some embodiments, the external medical device 800 may be wirelessly connected to the headset 822. The external medical device 800 may communicate, using wireless or wired communication technology, with other external devices such as a phone 825 or programmer 826.

Figure 9:
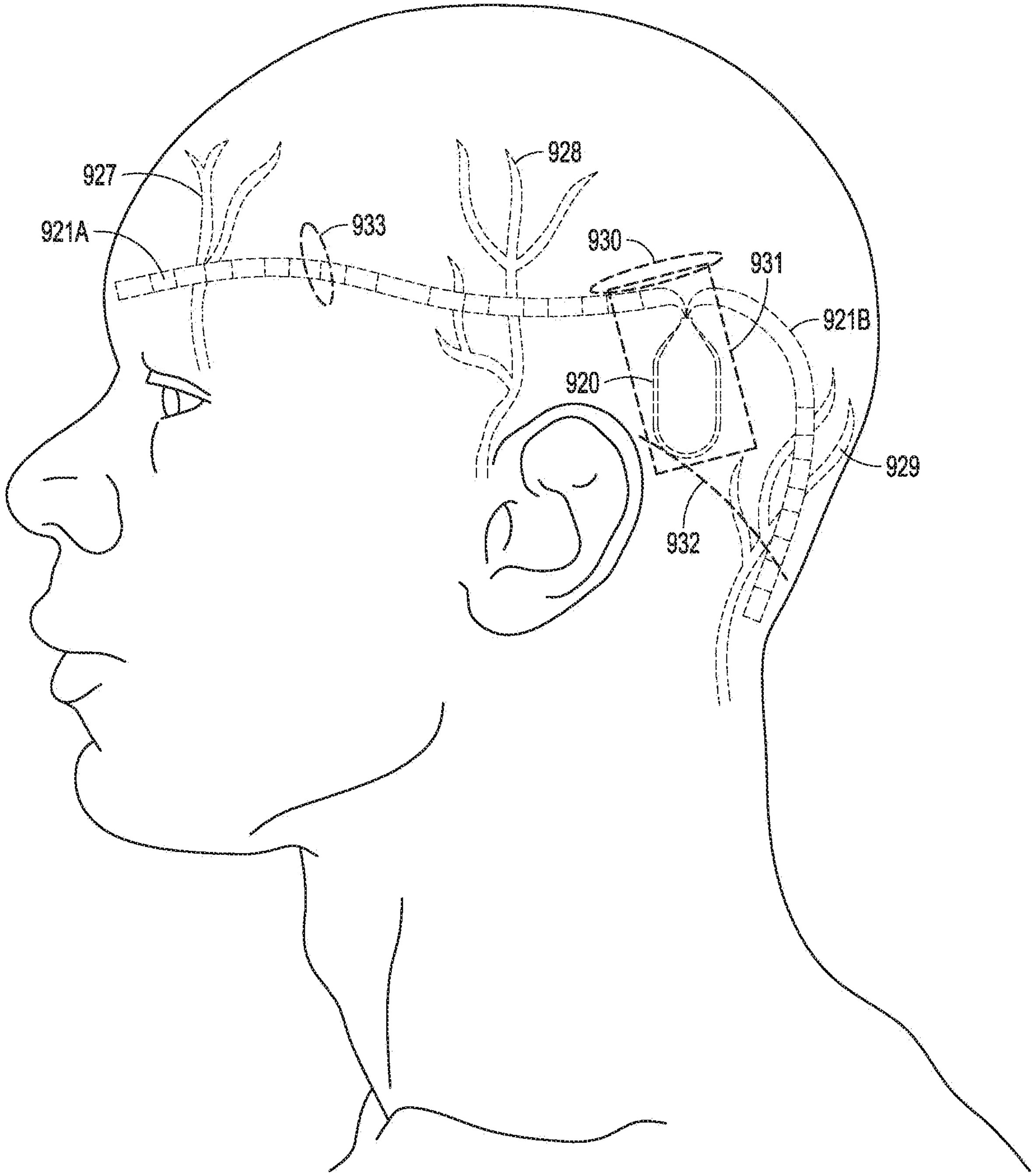
FIG. 9 illustrates, by way of example and not limitation, a side view of fully head-located neurostimulation system.

FIG. 9 illustrates, by way of example and not limitation, a side view of fully head-located neurostimulation system. Also illustrated are the supraorbital nerve 927, the auriculotemporal nerve 928 and the occipital nerve 929. The illustrated system includes a medical device (e.g., pulse generator) 920 and both a first lead 921A and a second lead 921B attached to the medical device 920. The medical device 920 and leads 921A and 921B are configured for use in stimulating the supraorbital nerve 927 toward the front of the head and the occipital nerve 929 toward the back of the head.

The patient may have had a period of trial neurostimulation, which is standard in traditional neurostimulator evaluations but is optional here. The actual permanent implant may occur in a standard operating suite with appropriate sterile precautions. By way of example and not limitation, the patient may be prepped and draped. The patient may be administered prophylactic antibiotics, local anesthetic, and sedation. The patient may be placed in a supine position with a head of the bed elevated to approximately thirty degrees. The patient's head may be turned to better access the intended implant location. While the implantable medical device may be positioned subcutaneously anywhere, it may be positioned above and behind the ear in this illustrated embodiment. Thus, a first incision 930 of sufficient length (approximately 4-6 cm) is made to a depth sufficient to reach the subcutaneous layer. A pocket 931 to accept the medical device 920 is fashioned by standard dissection techniques. The pocket 931 may be directed below the incision. The pocket 931 may be angled depending on the desired orientation of the medical device. For example, the pocket 931 may be angled posteriorly, as illustrated. The pocket 931 may be 10-20% larger than the medical device 920 to allow for a comfortable fit and no undue tension on the overlying skin and/or incision. The first incision 930 may be made and the pocket 931 formed so that the implantable medical device abuts against the nuchal ridge 932 when fully inserted into the pocket 931. The first incision 930 should not interfere with the implanted medical device 920. The present subject matter may use template(s) to help make the incision in a desired location.

A second incision 933 may be made to the subcutaneous layer at a point above and anterior to the pinna of the ear in the temple region to assist with subcutaneously routing the first lead 921A. The first lead 921A may be passed from the medical device 920 in the pocket 931 to the second incision 933, and then passed from the second incision 933 to its final subcutaneous position over supraorbital nerves 927. The second lead 921B may be passed from the medical device 920 in the pocket 931 back toward the occipital nerve 929. The medical device 920 may be inserted into the pocket 931 either before or after the leads 921A and/or 921B are tunneled to their final subcutaneous position to deliver therapy.

Tubular introducer(s) with a plastic-peel away shell may be used to assist with lead placement. However, other techniques may be used to subcutaneously tunnel the leads to their final placement to deliver the neurostimulation therapy. Following the entire placement of the complete system, including the medical device and both leads and suturing, the medical device may be powered-up and its circuits checked. Upon recovery from anesthesia the system may be turned on for the patient with a portable programmer and the multiple parameters for the system may be programmed to provide a desired therapy for the patient.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A medical system, comprising:

a patient-applied part configured to physically contact a patient during normal use;

a medical device, including:

a device housing;

a rechargeable battery within the device housing;

a control circuit within the device housing;

a power circuit within the device housing; and an electrical port on the device housing for use in making electrical connections to the control circuit and the power circuit within the device housing;

a power cable with a first end configured to be electrically connected to an electrical power line and a second end configured to be removably connected to the electrical port, and a patient-applied part cable with a first end configured to be electrically connected to the patient-applied part and a second end configured to be removably connected to the electrical port, wherein:

the electrical port is not able to be concurrently connected to both the power cable and the patient-applied part cable, the power circuit is configured to be electrically connected to the electrical power line via the power cable and to recharge the rechargeable battery using power from the electrical power line, the control circuit is configured to be powered by the rechargeable battery and is electrically connected to the patient-applied part via the patient-applied part cable during normal use when the patient-applied part is in physical contact with the patient, thereby enabling the medical system to diagnose, treat or monitor a patient or to compensate or alleviate a disease, an injury or a disability experienced by the patient, the medical system is designed for use in a home healthcare environment, and the electrical port includes a plurality of conductor connectors, wherein the plurality of conductor connectors includes exclusive first and second subsets, wherein the first subset is exclusively used to electrically connect the power circuit to the electrical power line via the power cable, and the second subset is exclusively used to electrically connect the control circuit to the patient-applied part, wherein the power cable is configured to make an electrical connection through the power cable to only the first subset of conductor connectors, and the patient-applied part cable is configured to make an electrical connection through the patient-applied part cable to only the second subset of conductor connectors.

2. The medical system of claim 1, wherein the patient-applied part includes a coil assembly configured for use to be placed on the patient and used to charge an implantable device.

3. The medical system of claim 1, wherein the patient-applied part includes a coil assembly configured for use to be placed on the patient and used to communicate with an implantable device.

4. The medical system of claim 1, wherein the patient-applied part includes at least one electrode configured to contact the patient.

5. The medical system of claim 4, wherein the at least one electrode is used to deliver an electrical therapy to the patient.

6. The medical system of claim 4, wherein the at least one electrode is used to sense an electrical signal from the patient.

7. The medical system of claim 1, wherein the medical device is configured to communicate with the patient-applied part.

8. The medical system of claim 1, wherein the patient-applied part includes a sensor configured to contact the patient during normal use.

9. The medical system of claim 1, wherein the first end of the patient-applied part cable is integrally connected to the patient-applied part.

10. The medical system of claim 1, wherein the first end of the patient-applied part cable is removably connected to the patient-applied part.

11. The medical system of claim 1, further comprising at least one implantable medical device, wherein the patient-applied part includes at least one coil assembly corresponding to the at least one implantable medical device and configured for use to charge, program, and/or communicate with the at least one implantable medical device, and the medical device is an external medical device, the patient-applied part cable is a coil assembly cable having the first end configured to be electrically connected to the at least one coil assembly, and the control circuit is electrically connected to the at least one coil assembly via the coil assembly cable during normal use when the at least one coil assembly is in physical contact with the patient.

12. The medical system of claim 11, wherein the at least one implantable device includes an implantable neurostimulator.

13. The medical system of claim 11, further comprising a headset, the headset including the at least one coil assembly.

14. The medical system of claim 13, wherein the headset includes at least one sensor, wherein the coil assembly cable is configured for use to make an electrical connection between the at least one sensor and the control circuit via the electrical port.

15. The medical system of claim 13, wherein the first end of the coil assembly cable is integrally connected to the headset.

16. The medical system of claim 11, wherein the second end of the power cable and the second end of the coil assembly cable have identical connectors configured to mate with the electrical port.

17. The medical system of claim 1, wherein the second end of the power cable and the second end of the patient-applied part cable have a same physical connector design configured to mate with the electrical port.

18. The medical system of claim 1, wherein the electrical port comprises a multi-pin connector having a predetermined shape, and wherein the device housing comprises a feature configured to accept the second end of the power cable and the second end of the patient-applied part cable in only one orientation.

19. A method performed in a healthcare facility or home healthcare environment using a medical system having a patient-applied part configured to physically contact a patient during normal use and a medical device, where the medical device includes a device housing, a rechargeable battery within the device housing, a control circuit within the device housing, a power circuit within the device housing, and an electrical port on the device housing for use in making electrical connections to the control circuit and the power circuit within the device housing, wherein the electrical port includes a plurality of conductor connectors, the plurality of conductor connectors including exclusive first and second subsets, wherein the first subset is exclusively used to electrically connect the power circuit to an electrical power line via a power cable, and the second subset is exclusively used to electrically connect the control circuit to the patient-applied part, the method comprising:

electrically connecting the patient-applied part to the control circuit during normal use when the patient applied-part is in physical contact with the patient, thereby enabling the medical system to diagnose, treat or monitor a patient or to compensate or alleviate a disease, an injury or a disability experienced by the patient, wherein a patient applied-part cable is used to electrically connect the patient-applied part to the control circuit, the patient applied-part cable having a first end configured to be electrically connected to the patient-applied part and a second end configured to be removably connected to the electrical port, the patient-applied part cable being configured to make an electrical connection through the patient-applied part cable to only the second subset of conductor connectors, charging the rechargeable battery using a power cable with a first end configured to be electrically connected to an electrical power line and a second end configured to be removably connected to the electrical port to make an electrical connection with the power circuit, the power cable being configured to make an electrical connection through the power cable to only the first subset of conductor connectors, wherein the electrical port is not able to be concurrently connected to both the power cable and the patient applied-part cable.

20. The method of claim 19, wherein the patient-applied part comprises a headset with at least one coil assembly configured for use to charge, program, and/or communicate with at least one implantable medical device, the patient-applied part cable comprises a coil assembly cable, and electrically connecting the patient-applied part to the control circuit comprises electrically connecting the headset to the control circuit when the headset is in physical contact with the patient and is being used to communicate with, program, and/or charge the at least one implantable medical device.

* * * * *